(12) United States Patent
Pugh et al.

(10) Patent No.: US 8,638,502 B2
(45) Date of Patent: Jan. 28, 2014

(54) LIQUID MENISCUS LENS WITH NON-SPHERICAL MENISCUS WALL

(75) Inventors: Randall B. Pugh, Jacksonville, FL (US); Daniel B. Otts, Jacksonville, FL (US); Adam Toner, Jacksonville, FL (US); Edward R. Kernick, Jacksonville, FL (US); James Daniel Riall, St. Johns, FL (US); Sharika Snook, St. Augustine, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 251 days.

(21) Appl. No.: 13/232,453

(22) Filed: Sep. 14, 2011

(65) Prior Publication Data

US 2012/0075711 A1    Mar. 29, 2012

Related U.S. Application Data

(63) Continuation-in-part of application No. 13/095,786, filed on Apr. 27, 2011, and a continuation-in-part of application No. 13/149,105, filed on May 31, 2011.

(60) Provisional application No. 61/387,510, filed on Sep. 29, 2010.

(51) Int. Cl.
*G02B 1/06* (2006.01)
*G02C 7/00* (2006.01)
*G02C 3/00* (2006.01)
*G02B 3/14* (2006.01)

(52) U.S. Cl.
CPC .................................. *G02B 3/14* (2013.01)
USPC .................. 359/665; 351/159.34; 351/159.68

(58) Field of Classification Search
USPC ......... 359/665, 666, 667; 351/159.34, 159.68
See application file for complete search history.

(56) References Cited

U.S. PATENT DOCUMENTS

2010/0020285 A1    1/2010    Berge

FOREIGN PATENT DOCUMENTS

| EP | 1674892 A1 | 6/2006 |
|---|---|---|
| EP | 1906213 A1 | 4/2008 |
| WO | WO 03069380 A1 | 8/2003 |
| WO | WO 2004077125 A2 | 9/2004 |
| WO | WO 2004077125 A3 | 9/2004 |
| WO | WO 2004099844 A1 | 11/2004 |
| WO | WO 2004099845 A1 | 11/2004 |
| WO | WO 2004099846 A1 | 11/2004 |
| WO | WO 2004102253 A1 | 11/2004 |
| WO | WO 2005069043 A1 | 7/2005 |
| WO | WO 2005069044 A1 | 7/2005 |
| WO | WO 2005088388 A1 | 9/2005 |
| WO | WO 2005096029 A1 | 10/2005 |
| WO | WO 2005096030 A1 | 10/2005 |
| WO | WO 2005109074 A1 | 11/2005 |
| WO | WO 2006123288 A2 | 11/2006 |
| WO | WO 2006123288 A3 | 11/2006 |
| WO | WO 2011143554 A1 | 11/2011 |

OTHER PUBLICATIONS

PCT International Search Report, dated Dec. 29, 2011, for PCT Intl. Appln. No. PCT/US2011/053414.

*Primary Examiner* — Jack Dinh (57) ABSTRACT

The present invention relates generally to an arcuate liquid meniscus lens with a meniscus wall. Some specific embodiments include a liquid meniscus lens with a meniscus wall essentially in the shape of a conical frustum, a cross section of which is non-spherical. Embodiments may also include a lens of suitable size and shape for inclusion in a contact lens.

30 Claims, 8 Drawing Sheets

LIQUID MENISCUS LENS WITH NON-SPHERICAL MENISCUS WALL

RELATED APPLICATIONS

This application claims priority to Provisional Patent Application U.S. Ser. No. 61/387,510 entitled, "LIQUID MENISCUS LENS WITH NON-SPHERICAL MENISCUS WALL", and as a Continuation in Part Application to Non-Provisional patent application U.S. Ser. No. 13/095,786 which was filed on Apr. 27, 2011 and entitled "ARCUATE LIQUID MENISCUS LENS", as well as Non-Provisional patent application U.S. Ser. No. 13/149,105 which was filed on Jun. 29, 2010 and entitled "LENS WITH CONICAL FRUSTUM MENISCUS WALL", as a Continuation in Part Application, the contents of each of which are relied upon and incorporated by reference.

FIELD OF USE

The present invention relates generally to a liquid meniscus lens, more specifically, it includes a liquid meniscus lens with a meniscus wall, a cross-section of which is non-spherical and may also be arcuate.

BACKGROUND

Liquid meniscus lenses have been known in various industries. As discussed more fully below with reference to FIGS. 1A and 1B, known liquid meniscus lenses were engineered in cylindrical shapes with a perimeter surface formed by points at a fixed distance from an axis which is a straight line. Known liquid meniscus lenses have been limited to designs with a first interior surface generally parallel to a second interior surface and each perpendicular to a cylindrical axis. Known examples of the use of liquid meniscus lenses include devices such as electronic cameras.

Traditionally, an ophthalmic device, such as a contact lens and an intraocular lens included a biocompatible device with a corrective, cosmetic or therapeutic quality. A contact lens, for example, can provide one or more of: vision correcting functionality; cosmetic enhancement; and therapeutic effects. Each function is provided by a physical characteristic of the lens. A design incorporating a refractive quality into a lens can provide a vision corrective function. A pigment incorporated into the lens can provide a cosmetic enhancement. An active agent incorporated into a lens can provide a therapeutic functionality.

More recently, electronic components have been incorporated into a contact lens. Some components can include semiconductor devices. However, physical constraints including the size, shape and control aspects of a liquid meniscus lens have precluded their use in an ophthalmic lens. Generally the cylindrical shape, sometimes referred to as the "hockey puck" shape of liquid meniscus lenses, has not been conducive to something that can work in a human eye environment.

In addition, a curved liquid meniscus lens includes physical challenges that are not necessarily present in a traditional design of a liquid meniscus lens with parallel sidewalls and/or optical windows.

SUMMARY

Accordingly, the present invention provides a liquid meniscus lens including an arcuate front curve lens and an arcuate back curve lens. Included in the present invention is a meniscus wall, a cross-section of which is non-spherical, with physical features conducive for one or both of attraction and repulsion of a liquid contained within the lens and forming a meniscus with another liquid.

According to the present invention, a first arcuate shaped optic is proximate to a second arcuate shaped optic with a cavity formed therebetween. A saline solution and an oil are maintained within the cavity. Application of electrostatic potential to a meniscus wall generally located in a perimeter area of one or both of the first arcuate optic and the second arcuate optic changes the physical shape of a meniscus formed between the saline solution and oil maintained within the cavity.

DETAILED DESCRIPTION OF THE INVENTION

The present invention provides for a liquid meniscus lens with at least one of a front curve lens and a back curve lens defining a meniscus cavity of the liquid meniscus lens.

GLOSSARY

In this description and claims directed to the presented invention, various terms may be used for which the following definitions will apply:

Contact Angle: The angle at which the oil/saline solution interface, also referred to as the liquid meniscus boundary, meets the meniscus wall. In the case of a linear meniscus wall, the contact angle is measured as the angle between the meniscus wall and the line tangent to the liquid meniscus boundary at the point where the liquid meniscus boundary meets the meniscus wall. In the case of a curved meniscus wall, the contact angle is measured as the angle between the lines tangent to the meniscus wall and the liquid meniscus boundary at the point where they meet.

Lens: As used herein, a Lens means an article with a front surface and a back surface that is optically transmissive to a predefined range of wavelengths of radiation, such as, by way of example, visible light. A lens may include one or both of a front surface and a back surface which are essentially flat or one or both of a front surface and a back surface which are arcuate in shape.

Liquid Meniscus Boundary: The arcuate surface interface between the saline solution and the oil. Generally, the surface will form a lens that is concave on one side and convex on the other.

Meniscus Cavity: The space in an arcuate liquid meniscus lens between the front curve lens and the back curve lens in which oil and saline solution are maintained.

Meniscus Wall: A specific area on the interior of the front curve lens, such that it is within the meniscus cavity, along which the liquid meniscus boundary moves.

Optical Zone: as used herein refers to an area of an ophthalmic lens through which a wearer of the ophthalmic lens sees.

Sharp: A geometric feature of an internal surface of either a front curve or back curve lens piece sufficient to contain the location of a contact line of two predefined fluids on the optic. The sharp is usually an outside corner rather than an inside corner. From a fluid standpoint it is an angle greater than 180 degrees.

Figure 1A:
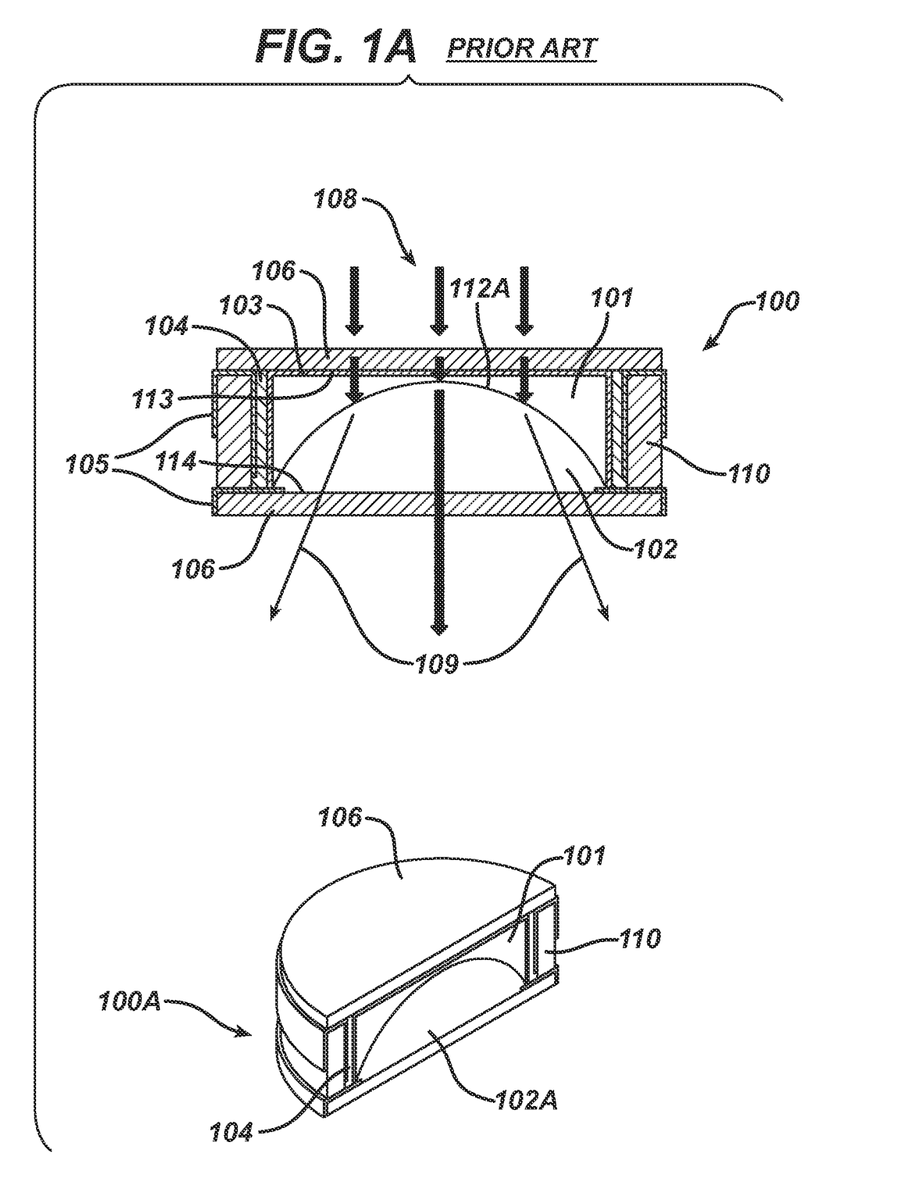
FIG. 1A illustrates a prior art example of a cylindrical liquid meniscus lens in a first state.

Referring now to FIG. 1A, a cut away view of a prior art lens 100 is illustrated with an oil 101 and a saline solution 102 contained within cylinder 110. The cylinder 110 includes two plates of optical material 106. Each plate 106 includes an essentially flat interior surface 113-114. The cylinder 110 includes an interior surface that is essentially rotationally symmetric. In some prior art embodiments, one or more surfaces may include a hydrophobic coating. Electrodes 105 are also included on or about the perimeter of the cylinder. An electrical insulator may also be used proximate to the electrodes 105.

According to the prior art, each of the interior surfaces 113-114 is essentially flat or planar. An interface surface 112A is defined between the saline solution 102A and the oil 101. As illustrated in FIG. 1A, the shape of the interface 112A is combined with the refractive index properties of the saline solution 102A and the oil 101 to receive incident light 108 through a first interior surface 113 and provide divergent light 109 through a second interior surface 114. The shape of the interface surface between the oil 101 and the saline solution 102 may be altered with the application of an electrical potential to the electrodes 105.

FIG. 100A illustrates a perspective view of the prior art lens illustrated at 100.

Figure 1B:
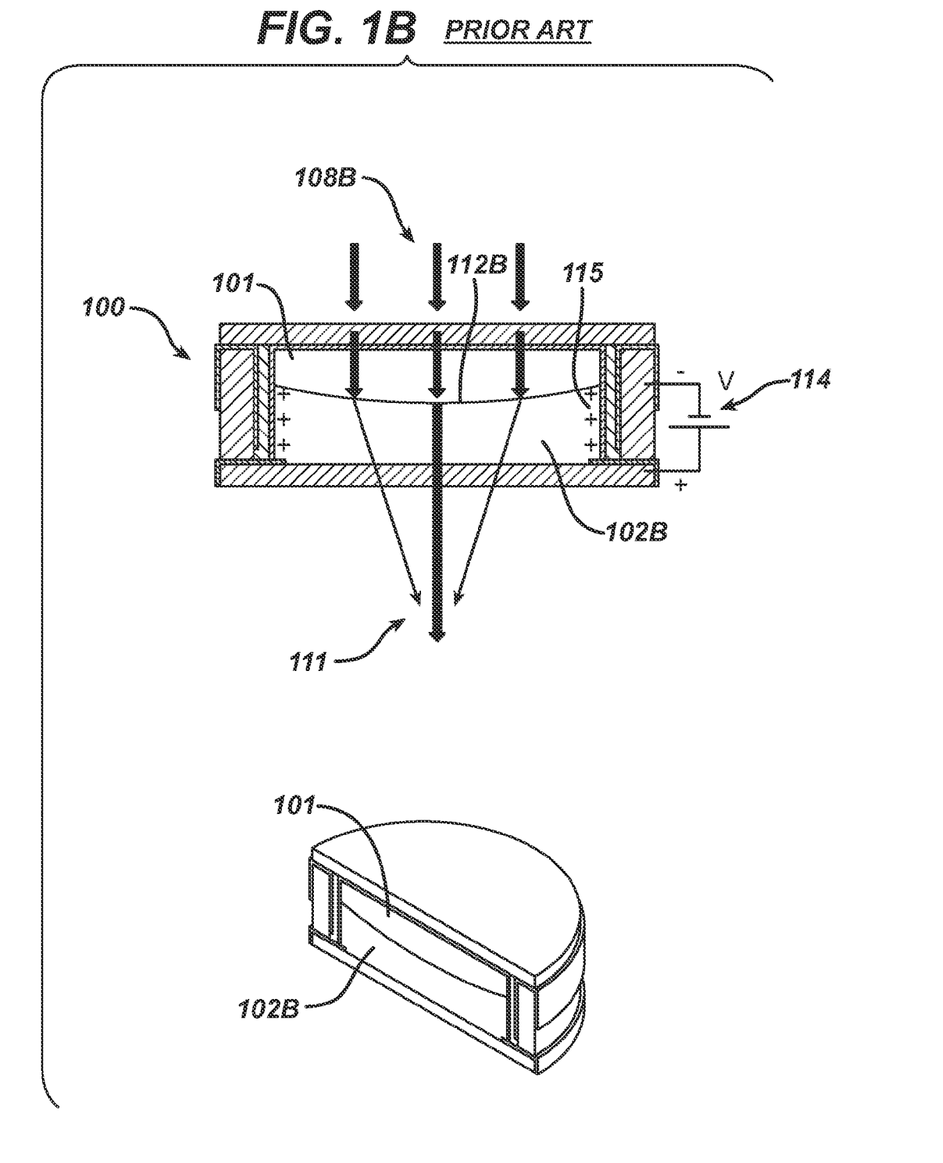
FIG. 1B illustrates the prior art example of a cylindrical liquid meniscus lens in a second state.

Referring now to FIG. 1B, the prior art lens 100 is illustrated in an energized state. The energized state is accomplished by applying voltage 114 across the electrodes 115. The shape of the interface surface 112B between the oil 101 and the saline solution 102B is altered with the application of an electrical potential to the electrodes 115. As illustrated in FIG. 1B, incident light 108B passing through the oil 101 and the saline solution 102B is focused into a convergent light pattern 111.

Figure 2:
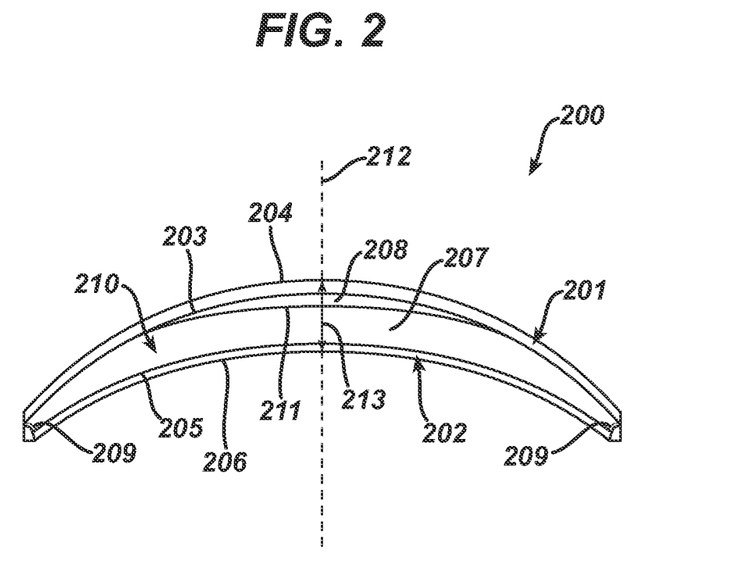
FIG. 2 illustrates a profile sliced cut away of an exemplary liquid meniscus lens according to some embodiments of the present invention.

Referring now to FIG. 2, a cut away view of a liquid meniscus lens 200 with a front curve lens 201 and a back curve lens 202. In various embodiments, the front curve lens 201 and the back curve lens 202 may include an arcuate lens or a substantially flat lens. In some preferred embodiments, the front curve lens 201 and the back curve lens 202 are positioned proximate to each other and form a cavity 210 therebetween. The front curve lens 201 includes a concave arcuate interior lens surface 203 and a convex arcuate exterior lens surface 204. The concave arcuate interior lens surface 203 may have one or more coatings (not illustrated in FIG. 2). Coatings may include, for example, one or more of electrically conductive materials or electrically insulating materials, hydrophobic materials or hydrophilic materials. One or both of the concave arcuate interior lens surface 203 and the coatings are in liquid and optical communication with an oil 208 contained within the cavity 210.

The back curve lens 202 includes a convex arcuate interior lens surface 205 and a concave arcuate exterior lens surface 206. The convex arcuate interior lens surface 205 may have one or more coatings (not illustrated in FIG. 2). Coatings may include, for example, one or more of electrically conductive materials or electrically insulating materials, hydrophobic materials or hydrophilic materials. At least one of the convex arcuate interior lens surface 205 and the coatings are in liquid and optical communication with a saline solution 207 contained within the cavity 210. The saline solution 207 includes one or more salts or other components which are ionically conductive and as such may be either attracted to or repulsed by an electric charge.

According to the present invention, an electrically conductive coating 209 is located along at least a portion of a periphery of one or both of the front curve lens 201 and the back curve lens 202. The electrically conductive coating 209 may include gold or silver and is preferably biocompatible. Application of an electrical potential to the electrically conductive coating 209 creates either an attraction or a repulsion of the ionically conductive salts or other components in the saline solution 207.

The front curve lens 201 has an optical power in relation to light passing through the concave arcuate interior lens surface 203 and a convex arcuate exterior lens surface 204. The optical power may be 0 or may be a plus or minus power. In some preferred embodiments, the optical power is a power typically found in corrective contact lenses, such as, by way of non-limiting example, a power between −8.0 and +8.0 diopters.

The back curve lens 202 has an optical power in relation to light passing through the convex arcuate interior lens surface 205 and a concave arcuate exterior lens surface 206. The optical power may be 0 or may be a plus or minus power. In some embodiments, the optical power is a power typically found in corrective contact lenses, such as, by way of non-limiting example, a power between −8.0 and +8.0 diopters. An optical axis 212 is formed through the back curve lens 202 and the front curve lens 201.

Various embodiments may also include a change in optical power associated with a change in shape of a liquid meniscus 211 formed between the saline solution 207 and the oil 208. In some embodiments, a change in optical power may be relatively small, such as, for example, a change of between 0 to 2.0 diopters of change. In other embodiments, a change in optical power associated with a change in shape of a liquid meniscus may be up to about 30 or more diopters of change. Generally, a higher change in optical power associated with a change in shape of a liquid meniscus 211 is associated with a relatively increased lens thickness 213.

According to some embodiments of the present invention, such as those embodiments that may be included in an ophthalmic lens, such as a contact lens, a cross cut lens thickness 213 of an arcuate liquid meniscus lens 200 will be up to about 1,000 microns thick. An exemplary lens thickness 213 of a relatively thinner lens 200 may be up to about 200 microns thick. Preferred embodiments may include a liquid meniscus lens 200 with a lens thickness 213 of about 600 microns thick. Generally a cross cut thickness of front curve lens 201 may be between about 35 microns to about 200 microns and a cross cut thickness of a back curve lens 202 may also be between about 35 microns and 200 microns. Typically, a cross-sectional profile includes a defined variance in thickness at different locations in the lens 200.

According to the present invention, an aggregate optical power is an aggregate of optical powers of the front curve lens 201 the back curve lens 202 and a liquid meniscus 211 formed between the oil 208 and the saline solution 207. In some embodiments, an optical power of the lens 200 will also include a difference in refractive index as between one or more of the front curve lens 201, the back curve lens 202, the oil 208 and the saline solution 207.

In those embodiments that include an arcuate liquid meniscus lens 200 incorporated into a contact lens, it is additionally desirous for the saline 207 and oil 208 to remain stable in their relative positions within the arcuate liquid meniscus lens 200 as a contact wearer moves. Generally, it is preferred to prevent the oil 208 from floating and moving relative to the saline 207 when the wearer moves. Accordingly, an oil 208 and saline solution 207 combination is preferably selected with a same or similar density. Additionally, an oil 208 and a saline solution 207 preferably have relatively low miscibility so that the saline solution 207 and oil 208 will not mix.

In some preferred embodiments, a volume of saline solution 207 contained within the cavity 210 is greater than the volume of oil 208 contained within the cavity 210. Additionally, some preferred embodiments include the saline solution 207 in contact with essentially an entirety of an interior surface 205 of the back curve lens 202. Some embodiments may include a volume of oil 208 that is about 66% or more by volume as compared to an amount of saline solution 207. Some additional embodiments may include an arcuate liquid meniscus lens wherein a volume of oil 208 is about 90% or less by volume as compared to an amount of saline solution 207.

Figure 3:
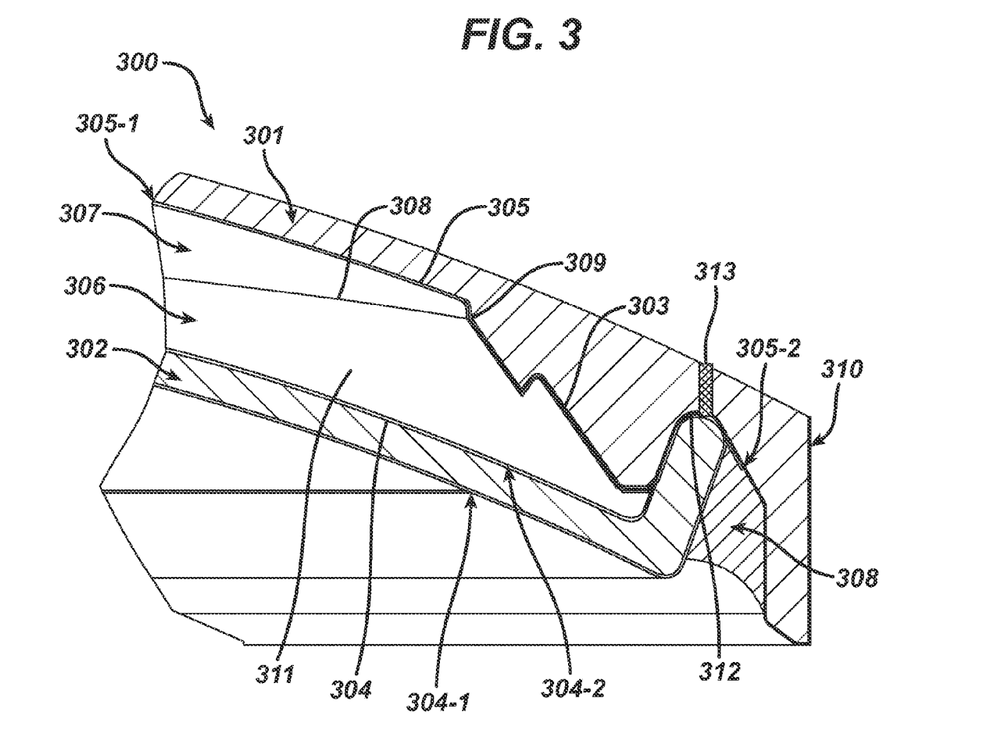
FIG. 3 illustrates a cross section of a portion of an exemplary arcuate liquid meniscus lens, according to some embodiments of the present invention.

Referring now to FIG. 3, a cutaway of an edge portion of an arcuate liquid meniscus lens 300 is illustrated. As discussed above, an arcuate liquid meniscus lens 300 includes combined front curve lens 301 and back curve lens 302 components. The front curve lens 301 and back curve lens 302 may be formed with one or more materials that are at least partially transparent. In some embodiments, one or both of the front curve lens 301 and the back curve lens 302 include generally optically clear plastic, such as for example, one or more of: PMMA, Zeonor and TPX.

One or both of the front curve lens 301 and the back curve lens 302 may be fashioned, for example via processes such as one or more of: single point diamond turning lathing; injection molding; digital mirror device free forming.

One or both of the front curve lens 301 and the back curve lens 302 may include a conductive coating 303, as illustrated, the conductive coating 303 extending along a perimeter portion from 309 to 310. In some preferred embodiments, a conductive coating 303 includes gold. The gold may be applied via a sputter process, vapor deposition or other known process. Alternative conductive coating 303 may include, by way of non-limiting example, aluminum, nickel, and indium tin oxide. Generally, the conductive coating 303 will be applied to perimeter areas of one or both of the front curve lens 301 and the back curve lens 302.

In some embodiments of the present invention, a back curve lens 302 has a conductive coating 304 applied to specific areas. For example, portions about the perimeter of the back curve lens 302 may be coated from a first boundary 304-1 to a second boundary 304-2. The gold coatings may be applied for example via a sputter process or a vapor deposition. In some embodiments, a mask may be used to apply the gold or other conductive material in a predetermined pattern around one or more perimeter portions of a front curve lens 301 or a back curve lens 302. Alternative conductive materials may be applied using various methods and covering varying areas of the back curve lens 302.

In some embodiments, a conductive pass through, such as, for example one or more holes or slots in a back curve lens 302 may be filled with a conductive filler material, such as, for example, a conductive epoxy. The conductive filler may provide electrical communication to a conductive coating on an interior surface of one or both of the front curve lens 301 and the back curve lens 302.

In another aspect of the present invention, one or both of the front curve lens 301 and the back curve lens 302 may be created from multiple different materials wherein an optical zone generally in a central area of the front curve lens 301 and the back curve lens 302 (not illustrated) may include an optically transparent material and a peripheral zone may include an optically opaque area that includes an electrically conductive material. The optically opaque area may also include one or more of control circuitry and energy sources.

In still another aspect, in some embodiments, an insulator coating 305 is applied to a front curve lens 301. By way of non-limiting example, the insulator coating 305 may be applied in an area from a first region 305-1 and extend to a second region 305-2. Insulators may include, for example, Parylene C™, Teflon AF or other materials with various electrical and mechanical characteristics and electrical resistance.

In some specific embodiments, an insulator coating 305 creates a boundary area to maintain separation between the conductive coating 303 and a saline solution 306 contained in a cavity between the front curve lens 301 and the back curve lens 302. Some embodiments accordingly include an insulator coating 305 patterned and positioned in one or more areas of one or both of the front curve lens 301 and the back curve lens 302 to prevent a positively charged conductor 303 and negatively charged saline solution 306 from coming into contact, wherein contact of a conductor 303 and a saline solution 306 will result in an electrical short circuit. Embodiments may include a positively charged saline solution 306 and a negatively charged conductor 303.

Still other embodiments may allow for a short circuit between a conductor 303 and a saline solution 306 as a reset function of circuitry associated with the operation of the lens 300. For example, a short circuit condition may equalize potential applied to the lens and cause the saline solution 306 and the oil 307 to revert to a default position.

Some preferred embodiments include a conductor 303 that extends from an area 309 on the interior of the cavity 311 to an area 310 external to the cavity 311. Other embodiments may include a channel 312 through the front curve lens or the back curve lens which may be filled with a conductive material 313, such as, for example, a waterproof conductive epoxy. The conductive material 313 may form or be connected to an electrical terminal external to the cavity. An electrical potential may be applied to the terminal and conducted to the coating via the conductive material 313 in the channel 312.

The thickness of the insulator coating 305 may be varied as a parameter of lens performance. According to the present invention, charged components, including the saline solution 306 and the conductor 303, are generally maintained on either side of the insulator coating 305. The present invention provides for an indirect relationship between the thickness of the insulator coating 305 and an electrical field between the saline solution 306 and the conductor 303, wherein the farther apart the saline solution 306 and the conductor 303 are maintained, the weaker the electrical field will be.

Generally, the present invention provides that electrical field strength may fall off dramatically as insulator coating 305 thickness increases. The closer together the fields are, the more energy that will generally be available to move a spherical liquid meniscus boundary 308. As a distance between the saline solution 306 and conductor 303 increases, the farther apart electrostatic charges of the saline solution 306 and the conductor coating 303 will be and therefore the harder it is to get the spherical liquid meniscus boundary 308 to move.

Inversely, the thinner the insulator coating 305, the more susceptible is the lens to defects in an insulator coating 305. Generally, even a relatively small hole in the insulator coating 305 will create an electrical short circuit and the lens will not function in an electrowetting fashion.

In some embodiments, it is desirable to include a saline solution 306 with density that is generally the same density of an oil 307 also contained within the lens 300. For example, a saline solution 306 may preferably include a density that is within 10% of a density of an oil 307 and more preferably the saline solution 306 will include a density within 5% of a density of an oil and most preferably within about 1% or less. In some embodiments, a concentration of salts or other components within the saline solution 306 may be adjusted to adjust the density of the saline solution 306.

According to the present invention, an arcuate liquid meniscus lens 300 will provide a more stable optical quality by limiting movement of the oil 307 in relation to the front curve lens 301 and the back curve lens 302. One method of maintaining stability of movement of the oil 307 in relation to one or both of the arcuate front curve lens 301 and the back curve lens 302 is to maintain a relatively congruent density in the oil 307 and the saline solution 306. In addition, due to the curve design of the interior surfaces of both the front curve lens 301 and the back curve lens 302, the relative depth or thickness of a layer of saline solution 306 is diminished as compared to a traditional cylindrical lens design. In this scenario, the interfacial forces acting on fluids within the cavity may have a relatively greater contribution toward maintaining an unperturbed liquid meniscus boundary 308. Consequently, the density matching requirement may become more relaxed in such cases. In some embodiments, the relative thinness of the fluid layers further supports the liquid lens boundary 308.

In some preferred embodiments, the saline solution 306 provides a low refractive index as compared to the oil 307 which provides a relatively high refractive index. However, in some embodiments it is possible to include a saline solution 306 with a higher refractive index as compared to the oil 307 which in such cases provides a relatively lower refractive index.

An adhesive 314 may be used to secure the front curve lens 301 and back curve lens 302 in place proximate to each other, thereby retaining the oil 307 and saline solution 306 therebetween. The adhesive 314 acts as a seal so that there is no leakage of saline solution 306 or oil 307 from the curved liquid meniscus lens 300.

Figure 4:
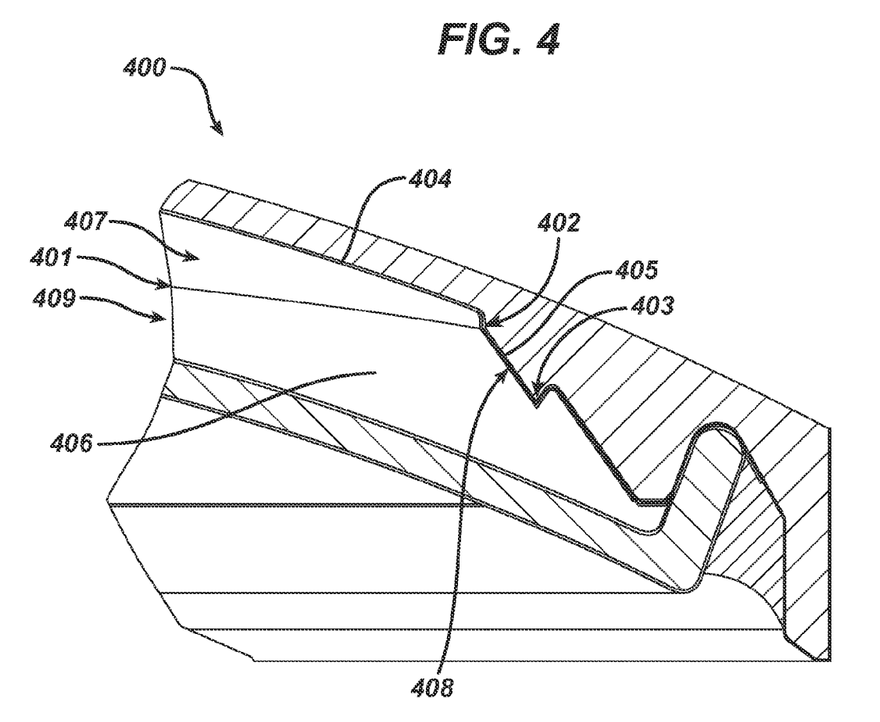
FIG. 4 illustrates additional exemplary aspects of an arcuate liquid meniscus lens.

Referring now to FIG. 4, a curved liquid meniscus lens 400 is illustrated with a liquid meniscus boundary 401 between the saline solution 406 and oil 407. According to some preferred embodiments, a meniscus wall 405 is defined in the front curve lens 404 by a first angular break in an arcuate wall extending between 402 and 403. The liquid meniscus boundary 401 will move up and down the meniscus wall 405 as electrical potential is applied and removed along one or more conductive coatings or conductive materials 408.

In some preferred embodiments, a conductive coating 408 will extend from an area internal to the cavity 409 holding the saline solution 406 and the oil 407 to an area external to the cavity 409 containing the saline solution 406 and oil 407. In such embodiments, the conductive coating 408 may be a conduit of an electrical potential applied to the conductive coating 408 at a point external to the cavity 409 to an area of the conductive coating 408 within the cavity 409 and in contact with the saline solution 406.

Figure 5:
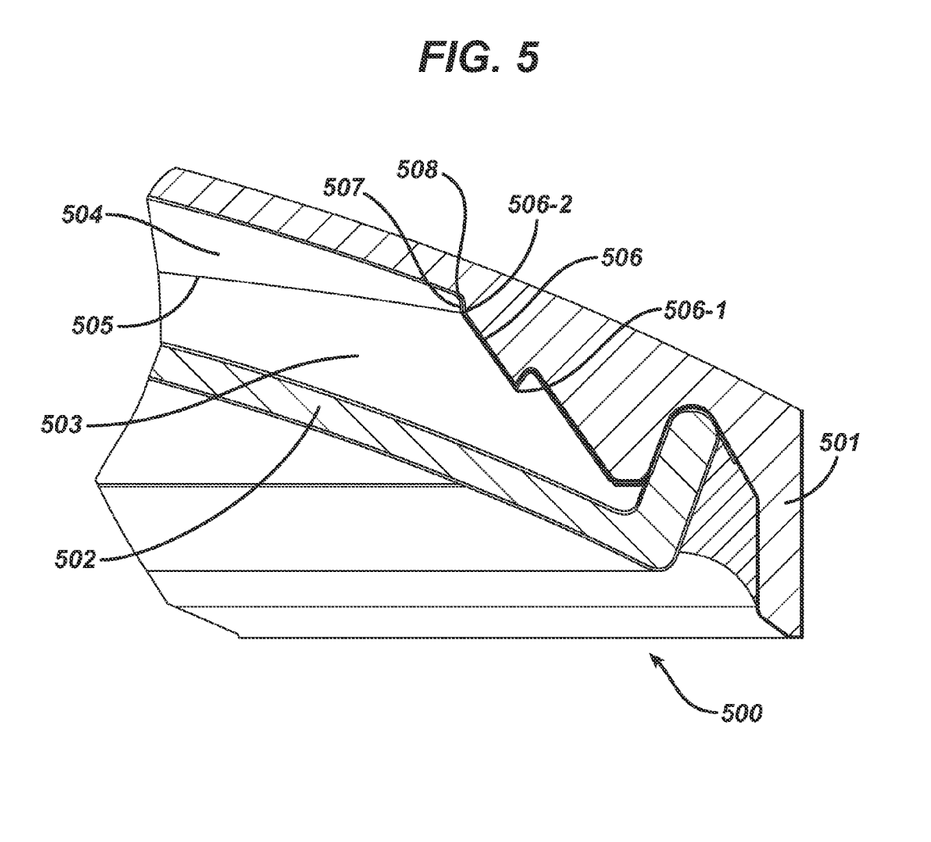
FIG. 5 illustrates meniscus wall elements within an arcuate liquid meniscus lens, according to some embodiments of the present invention.

Referring now to FIG. 5, a cut away view of an edge portion of an arcuate liquid meniscus lens 500 is shown with a front curve lens 501 and a back curve lens 502. The arcuate liquid meniscus lens 500 may contain saline solution 503 and oil 504. The geometry of the arcuate liquid meniscus lens 500 and the characteristics of the saline solution 503 and oil 504 facilitate formation of a liquid meniscus boundary 505 between the saline solution 503 and oil 504.

Generally, a liquid meniscus lens may be viewed as a capacitor with one or more of: conductive coatings, insulator coatings, pathways, and materials present on or through the front curve lens 501 and back curve lens 502. According to the present invention, a shape of a liquid meniscus boundary 505 and therefore a contact angle between the liquid meniscus boundary 505 and the front curve lens 501 change in response to an electrical potential applied to a surface of at least a portion of one or both of the front curve lens 501 and the back curve lens 502.

According to the present invention, a change in an electrical potential applied to the saline solution 503 via the conductive coatings or materials changes a position of the liquid meniscus boundary 505 along a meniscus wall 506. The movement takes place between a first sharp 506-1 and a second sharp 506-2.

In preferred embodiments, the liquid meniscus boundary 505 will be at or near the first sharp 506-1 when a first magnitude of electrical potential is applied to the lens, such as, for example, a voltage and current correlating with an unpowered state or resting state.

Application of a second magnitude of electrical potential, sometimes referred to as a first powered state, may correlate with a movement of the liquid meniscus boundary 505 along the meniscus wall 506 generally in the direction of the second sharp 506-2, causing the shape of the liquid meniscus boundary to change.

An applied voltage for transitioning between a first powered state and a second powered state may include, for example, a direct current voltage of between about 5 volts to about 60 volts. In other embodiments an alternating current voltage may also be utilized.

In some embodiments, the meniscus wall 506 will be a smooth surface in relation to the thickness of the insulator coating. A smooth meniscus wall 506 surface may minimize defects in the insulator coating. Additionally, because random irregularities in surface texture may result in uneven fluid motion and therefore cause uneven or unpredictable meniscus motion when energizing or de-energizing the lens, a smooth meniscus wall 506 is preferred. In some preferred embodiments, a smooth meniscus wall includes a peak to valley measurement along the meniscus wall 506 in the range of between about 1.25 nanometers to 5.00 nanometers.

In another aspect, in some embodiments, it is desirable for the meniscus wall 506 to be hydrophobic, in which case a defined texture, such as a nano-textured surface, may be incorporated in the design of the arcuate liquid meniscus lens.

In still another aspect, in some embodiments, the meniscus wall 506 may be angled relative to an optical axis of the lens. The angle can range from 0°, or parallel to the optical axis, to at or near 90°, or perpendicular to the optical axis. As illustrated, and in some preferred embodiments, the meniscus wall 506 angle is generally between about 30° and 50° in order for the arcuate liquid meniscus lens to function given the current contact angle between the liquid meniscus boundary 505 and the insulator-coated meniscus wall 506. With the use of different materials or with different optical objectives, such as telescopic vision, the angle of the meniscus wall 506 may be closer to 0° or 90°.

According to the present invention, an angle of a meniscus wall 506 may be designed to accommodate a magnitude of movement along a meniscus wall 506 upon application of a specified electrical voltage. In some embodiments, as meniscus wall 506 angle increases, the ability to change lens power generally decreases within given lens size and voltage parameters. Additionally, if the meniscus wall 506 is at or near 0° relative to the optical axis, the liquid meniscus boundary 505 will be steered nearly straight onto the front optic. Meniscus wall angle is one of several parameters that can be tailored to provide various outcomes in lens performance.

In some preferred embodiments, the meniscus wall 506 is approximately 0.265 mm in length. However, the angle of the meniscus wall 506 together with the size of the overall lens will naturally affect meniscus wall 506 length in various designs.

It may generally be considered that an arcuate liquid meniscus lens 500 will fail if the oil 504 contacts the back curve lens 502. Therefore, in preferred embodiments, the meniscus wall 506 is designed to allow a minimum clearance of 50 microns between the first sharp 506-1 and the back curve lens 502 at its nearest point. In other embodiments, the minimum clearance may be less than 50 microns, although the risk of lens failure increases as the clearance is reduced. In yet other embodiments, the clearance may be increased to mitigate the risk of lens failure, but the overall lens thickness will also increase which may be undesirable.

In still another aspect of some preferred embodiments of the present invention, the behavior of a liquid meniscus boundary 505 as it travels along a meniscus wall 506 may be extrapolated using Young's Equation. Although Young's Equation defines the balance of forces caused by a wet drop on a dry surface and assumes a perfectly flat surface, the fundamental properties can be applied to the electrowetted lens environment created within the arcuate liquid meniscus lens 500.

A first magnitude of electrical energy may be applied to the lens, such as, for example, when the lens is in an unpowered state. During the application of the first magnitude of electrical energy, a balance of interfacial energies between the oil 504 and saline solution 503 is achieved. Such a state may be referred to herein as a liquid meniscus boundary 505. The oil 504 and meniscus wall 506, and the saline solution 503 and meniscus wall 506, form an equilibrium contact angle between the liquid meniscus boundary 505 and the meniscus wall 506. When a change in magnitude of voltage is applied to the arcuate liquid meniscus lens 500, the balance of interfacial energies will change, resulting in a corresponding change in contact angle between the liquid meniscus boundary 505 and the meniscus wall 506.

The contact angle of the liquid meniscus boundary 505 with the insulator-coated meniscus wall 506 is an important element in the design and function of the arcuate liquid meniscus lens 500 not only due to its role in the Young's Equation in movement of the liquid meniscus boundary 505, but also because the contact angle is used in conjunction with other features of the arcuate liquid meniscus lens 500 to limit meniscus movement.

Discontinuities, such as sharps 506-1 and 506-2, at both ends of the meniscus wall 506 act as boundaries for liquid meniscus 505 movement because it would require a significant change in applied electrical potential to effect a large enough change in liquid meniscus contact angle to move the liquid meniscus boundary 505 past one of the sharps. By way of non-limiting example, in some embodiments, a contact angle of the liquid meniscus boundary 505 with the meniscus wall 506 is in the range of 15° to 40° whereas the contact angle of the liquid meniscus boundary 505 with the step 507 beyond the second sharp 506-2 is perhaps in the range of 90° to 130° and in some preferred embodiments about 110°.

A voltage may be applied to the lens, resulting in movement of the liquid meniscus boundary 505 along the meniscus wall 506 toward the second sharp 506-2. The natural contact angle of the liquid meniscus boundary 505 with the insulator-coated meniscus wall 506 will cause the liquid meniscus boundary 505 to stop at the second sharp 506-2 unless significantly more voltage is supplied.

At one end of the meniscus wall 506, a first sharp 506-1 generally defines one limit beyond which the liquid meniscus boundary 505 will not typically move. In some embodiments, the first sharp 506-1 is constructed as a sharp edge. In other preferred embodiments, the first sharp 506-1 has a defined small radial surface which can be created with less possibility of defect. Conductive, insulator, and other possible desired coatings may not deposit evenly and predictably on a sharp edge, whereas a defined radius edge of the radial surface can be coated more reliably.

In some embodiments, the first sharp 506-1 is constructed at about a 90° angle with a defined radius of about 10 microns. The sharp may also be created with less than a 90° angle. In some embodiments, a sharp with a larger angle than 90° may be used to increase the sturdiness of the sharp, but the design would then take up more lens space.

In various embodiments, a defined radius of a sharp 506-1 and/or 506-2 may be in the range of 5 microns to 50 microns. A larger defined radius may be used to improve the reliability of the coatings, but at the cost of using more space within the tight confines of the lens design. In this, as in many other areas of lens design, tradeoffs exist between ease of construction, optimization of lens functions, and minimizing size. A functional, reliable arcuate liquid meniscus lens 500 may be made using a wide range of variables.

In some embodiments, a larger sharp radius may be used in conjunction with an improved surface finish on a side-wall between two adjacent sharps. In some embodiments, it may be desirable that a surface from a first radius (sharp) to a second radius (sharp) be smooth and without discontinuities wherein it is helpful to cut a mold used to fashion a sharp with the same tool. Radii included in a sharp may be cut into a mold tool surface, wherein the mold tool surface radius is larger than the sharp radius. Wherein the mold tool surface is a continuous surface including one or more sharps and a side wall. A larger tool radius may generally relate to a smoother surface finish of a corresponding cut.

A second sharp 506-2, includes a feature designed to limit oil movement when voltage is applied to the arcuate liquid meniscus lens 500. The second sharp 506-2 may also include, in some embodiments a generally pointed end, or in other embodiments, the second sharp 506-2 may include a defined radius of between 5 and 25 microns, most preferred 10 microns. A 10 micron radius performs well as a sharp and can be created using single point diamond turning lathe or injection molding processes.

A vertical or nearly vertical step 507, extending to a start of the optical area 508 of the front curve lens 501 may be included on a side of the second sharp 506-2 opposing the meniscus wall 506. In some embodiments, the step 507 is 120 microns in height, although it could be in the range of 50 to 200 microns.

In some embodiments, the step 507 may be angled at about 5° from optical axis. In other embodiments, the step 507 angle may be as little as 1° or 2° or may be angled more than 5°. A step 507 that is less angled from optical axis will generally act as a more effective limiter of meniscus movement because it would require a greater change in the contact angle of the liquid meniscus boundary 505 to move off of the meniscus wall 506 and onto the step 507. The transition from the step 507 to the start of the optical area 508 is a 25 micron radius. A larger radius would unnecessarily consume more space within the lens design. A smaller radius is possible and may be implemented if necessary to gain space. The decision to use a defined radius rather than a theoretical sharp in this area as well as others in the lens is based, in part, on the potential move to an injection molding process for lens elements. A curve between the step 507 and the start of the optical area 508 will improve plastic flow during the injection molding process and result in a lens with optimal strength and stress-handling characteristics.

Figure 6:
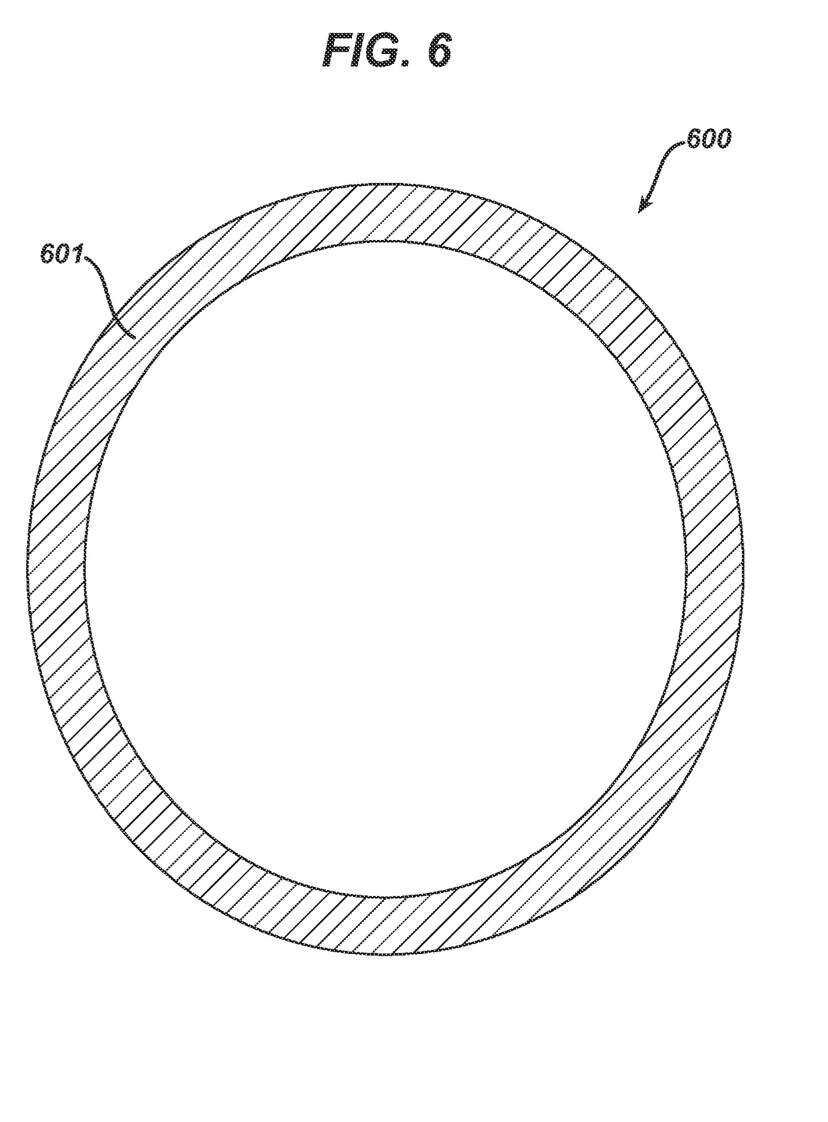
FIG. 6 illustrates a top down sectional view of a non-spherical meniscus wall in an arcuate liquid meniscus lens.

Referring now to FIG. 6, depicted is a top-down sectional view of a non-spherical meniscus wall 601 component of an arcuate liquid meniscus lens. In FIG. 6, the shape of the non-spherical meniscus wall 601 is exaggerated for emphasis. If drawn using a realistic scale, FIG. 6 would show a meniscus wall with a very slight non-spherical shape such that it would appear spherical to the unaided eye. In most preferred embodiments the non-spherical meniscus wall is created in an elliptical form. A toric shaped lens may thereby be created with a slightly elliptical liquid meniscus.

A preferred embodiment includes the non-spherical meniscus wall 601 in a spherical arcuate liquid meniscus lens assembly. Other embodiments incorporate the non-spherical meniscus wall 601 in a non-spherical arcuate liquid meniscus lens assembly.

Figure 7:
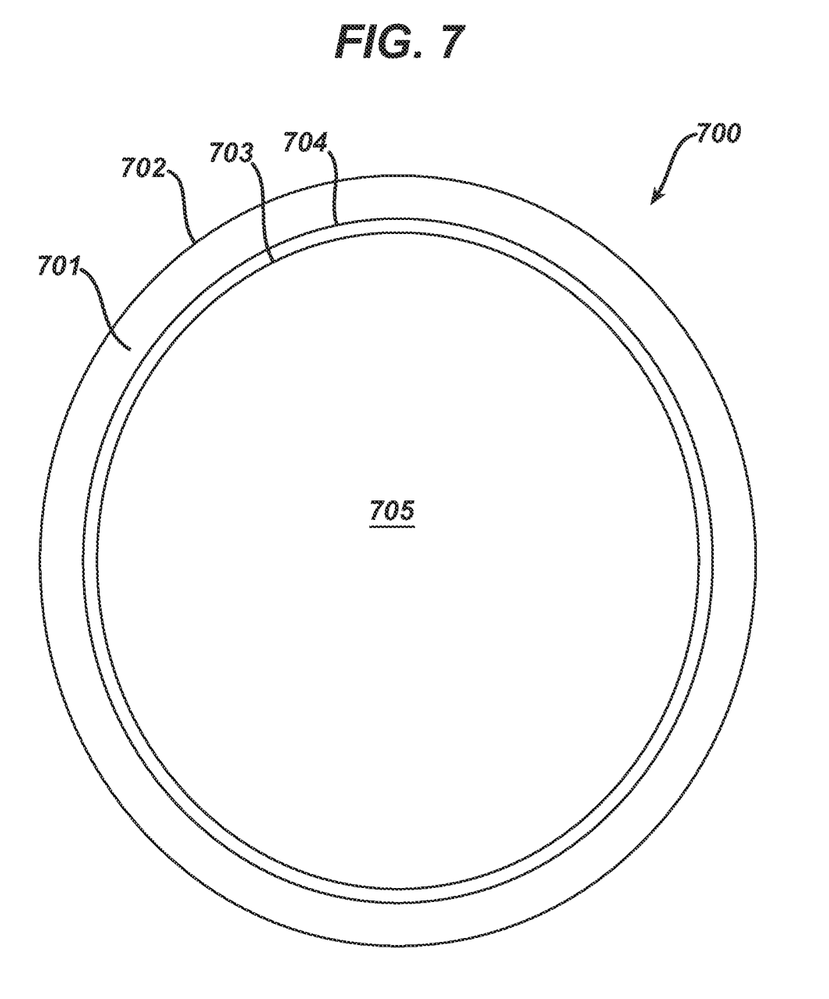
FIG. 7 illustrates a top down orthogonal view of a non-spherical meniscus wall in an arcuate liquid meniscus lens showing a position of the liquid meniscus.

Referring now to FIG. 7, a top-down orthogonal view of a non-spherical meniscus wall 701 in an arcuate liquid meniscus lens is portrayed including the first sharp 702, second sharp 703 and optical area 704. The magnitude of the ellipse is again emphasized in FIG. 7, as it was in FIG. 6. The liquid meniscus contacts the non-spherical meniscus wall 701 at line 705. In this depiction, the liquid meniscus contact line 705 is in a powered state, nearer to the second sharp 703. In an unpowered state, the liquid meniscus contact line 705 would be at or nearer the first sharp 702.

Utilizing a meniscus wall that is elliptical in construct, allows the cavity between the first and second arcuate shaped optics to be non-spherical and the resulting oil and saline solution takes the form of a segment of a torus. The resulting lens includes cylinder power, axis and optical power capable of correcting astigmatism. Specific cylinder powers are achieved by varying the magnitude of the ellipse of the meniscus wall. Axis is controlled by the degree of rotation at which the ellipse is aligned within the arcuate liquid meniscus lens assembly. In addition to astigmatism correction, a specific optical power for far vision may be achieved within the arcuate liquid meniscus lens with non-spherical meniscus wall when a first voltage level is applied, resulting in movement of the liquid meniscus to a first state. A second, higher, voltage level may be applied to further move the liquid meniscus, resulting in optical power correction for near vision. Alternatively, optical power correction for far vision may occur in a lens which encapsulates the arcuate liquid meniscus lens, while astigmatism and near vision are corrected within the arcuate liquid meniscus lens with non-spherical meniscus wall.

The liquid meniscus lens with non-spherical meniscus wall includes various methods of lens stabilization to maintain the correct position of the lens on the eye for astigmatic correction. Stabilization is achieved using techniques such as ballasting or more advanced accelerated stabilization designs. The stabilization techniques are implemented within the arcuate liquid meniscus lens or in a lens that encapsulates the arcuate liquid meniscus lens.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

The invention claimed is:

1. An optical lens comprising:
   a front curve lens comprising a front curve lens exterior surface and a front curve lens interior surface, wherein both said front curve lens exterior surface and said front curve lens interior surface comprise an actuate shape;
   a back curve lens comprising a back curve lens interior surface and a back curve lens exterior surface, wherein both said back curve lens interior surface and the back curve lens exterior surface comprise an arcuate shape, said back curve lens positioned proximate to said front curve lens such that said front curve lens interior surface and said back curve lens interior surface form a cavity therebetween;
   a volume of saline solution and oil contained within the cavity formed between said front curve lens interior surface and said back curve lens interior surface, said volume of saline solution and oil comprising a meniscus therebetween; and
   a meniscus wall comprising a general shape of a conical frustum, wherein a cross section of the conical frustum is non-spherical.

2. The optical lens of claim 1 additionally comprising a conductive coating on at least a portion of said meniscus wall.

3. The optical lens of claim 2 wherein the volume of oil comprises a density about equal to a density of the saline solution.

4. The optical lens of claim 2 wherein the volume of oil comprises density within about 10% of a density of the saline solution.

5. The optical lens of claim 2 wherein the volume of oil comprises density within about 5% of a density of the saline solution.

6. The optical lens of claim 2 wherein the conductive coating extends from an area interior to the cavity to an area external to the cavity.

7. The optical lens of claim 6, wherein the area of conductive coating external to the cavity forms an electrical terminal for providing an electrical potential to the liquid meniscus lens.

8. The optical lens of claim 6 wherein the saline solution and the oil form a meniscus and an application of an electrical potential to the area of conductive coating external to the cavity causes a change in position of contact of the meniscus along the meniscus wall.

9. The optical lens of claim 6 wherein the electrical potential comprises a direct current.

10. The optical lens of claim 6 wherein the electrical potential comprises between about 5.0 volts to 60.0 volts.

11. The optical lens of claim 10 wherein the electrical potential comprises about 20.0 volts.

12. The optical lens of claim 10 wherein the electrical potential comprises about 5.0 volts.

13. The optical lens of claim 6 wherein the electrical potential comprises between about 3.5 volts to about 7.5 volts.

14. The optical lens of claim 1 wherein the volume of oil is less than the volume of saline solution contained within the cavity.

15. The optical lens of claim 14 wherein the front curve lens exterior surface comprises an optical power other than about 0.

16. The optical lens of claim 14 wherein the front curve lens interior surface comprises an optical power other than about 0.

17. The optical lens of claim 14 wherein the back curve lens exterior surface comprises an optical power other than about 0.

18. The optical lens of claim 14 wherein the back curve lens interior surface comprises an optical power other than about 0.

19. The optical lens of claim 14 additionally comprising a channel through one or both of the front curve lens and the back curve lens and a conductive material filling the channel.

20. The optical lens of claim 19 additionally comprising a terminal in electrical communication with the conductive material filling the channel.

21. The optical lens of claim 20 wherein application of an electrical potential to the terminal causes a change in the shape of the meniscus.

22. The optical lens of claim 14 additionally comprising an insulator coating along at least a portion of the interior surface of the front curve lens, wherein the insulator coating comprises an electrical insulator.

23. The optical lens of claim 22, wherein the insulator comprises one of Parylene C™ and Teflon AF.

24. The optical lens of claim 22 wherein the insulator comprises a boundary area to maintain separation between the conductive coating and a saline solution contained in the cavity between the front curve lens and the back curve lens.

25. The optical lens of claim 14 wherein an angle of the conical frustum comprising the meniscus wall comprises between about 30° and 50°.

26. The optical lens of claim 25 additionally comprising a meniscus sharp adjacent to the meniscus wall, said sharp comprising a angular feature for containing the volume of saline solution and oil.

27. The optical lens of claim 26 wherein the sharp comprises a radial surface portion.

28. The optical lens of claim 27 wherein the radial surface portion comprises a radius in the range of 5 microns to 25 microns.

29. The optical lens of claim 1 wherein the volume of oil comprises about 66% or more by volume as compared to an amount of saline solution.

30. The optical lens of claim 1 wherein the volume of oil comprises about 90% or less by volume as compared to an amount of saline solution.

* * * * *